US008206563B2

(12) United States Patent
Heller

(10) Patent No.: US 8,206,563 B2
(45) Date of Patent: Jun. 26, 2012

(54) DEVICE FOR THE DETERMINATION OF GLYCATED HEMOGLOBIN

(75) Inventor: Adam Heller, Austin, TX (US)

(73) Assignee: Abbott Diabetes Care Inc., Alameda, CA (US)

(*) Notice: Subject to any disclaimer, the term of this patent is extended or adjusted under 35 U.S.C. 154(b) by 1058 days.

(21) Appl. No.: 11/296,183

(22) Filed: Dec. 6, 2005

(65) Prior Publication Data

US 2006/0205029 A1 Sep. 14, 2006

Related U.S. Application Data

(63) Continuation of application No. 10/146,577, filed on May 14, 2002, now Pat. No. 7,005,273.

(60) Provisional application No. 60/377,886, filed on May 2, 2002, provisional application No. 60/291,361, filed on May 16, 2001.

(51) Int. Cl.
G01N 27/327 (2006.01)
(52) U.S. Cl. .................. 204/403.01; 205/777.5
(58) Field of Classification Search ............ 204/403.01, 204/403.14; 205/777.5, 792; 435/25, 14, 435/287.1, 7.9
See application file for complete search history.

(56) References Cited

U.S. PATENT DOCUMENTS

| | | | |
|---|---|---|---|
| 3,774,243 A | 11/1973 | Ng et al. | |
| 3,811,950 A | 5/1974 | Avampato et al. | |
| 3,861,397 A | 1/1975 | Rao et al. | |
| 4,117,202 A | 9/1978 | Beck | |
| 4,224,125 A | 9/1980 | Nakamura et al. | |
| 4,431,004 A | 2/1984 | Bessman et al. | |
| 4,490,464 A | 12/1984 | Gorton et al. | |
| 4,581,336 A | 4/1986 | Malloy et al. | |
| 4,806,468 A | 2/1989 | Wagner et al. | |
| 4,820,399 A | 4/1989 | Senda et al. | |
| 4,820,636 A * | 4/1989 | Hill et al. ............... | 435/14 |
| 5,126,247 A | 6/1992 | Palmer et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,478,754 A | 12/1995 | Brandt et al. | |
| 5,506,144 A | 4/1996 | Sundrehagen | |
| 5,593,852 A | 1/1997 | Heller et al. | |
| 5,609,749 A | 3/1997 | Yamauchi et al. | |
| 5,639,672 A * | 6/1997 | Burd et al. .............. | 436/525 |
| 5,651,869 A | 7/1997 | Yoshioka et al. | |
| 5,665,222 A | 9/1997 | Heller et al. | |
| 5,804,401 A | 9/1998 | Gardiol et al. | |
| 5,807,747 A | 9/1998 | Wallworth et al. | |
| 5,837,546 A | 11/1998 | Allen et al. | |
| 5,888,787 A | 3/1999 | Chen et al. | |
| 5,906,921 A | 5/1999 | Ikeda et al. | |
| 5,972,199 A | 10/1999 | Heller et al. | |
| 6,054,039 A * | 4/2000 | Shieh ..................... | 205/778 |
| 6,103,033 A | 8/2000 | Say et al. | |
| 6,120,676 A | 9/2000 | Heller et al. | |
| 6,134,461 A | 10/2000 | Say et al. | |
| 6,143,164 A | 11/2000 | Heller et al. | |
| 6,174,734 B1 | 1/2001 | Ito et al. | |
| 6,175,752 B1 | 1/2001 | Say et al. | |
| 6,262,264 B1 | 7/2001 | Buck, Jr. et al. | |
| 6,294,062 B1 | 9/2001 | Buck, Jr. et al. | |
| 6,294,281 B1 | 9/2001 | Heller | |
| 6,338,790 B1 | 1/2002 | Feldman et al. | |
| 6,352,824 B1 | 3/2002 | Buck, Jr. et al. | |
| 6,399,293 B1 | 6/2002 | Pachl et al. | |
| 6,436,255 B2 | 8/2002 | Yamamoto et al. | |
| 6,500,571 B2 | 12/2002 | Liberatore et al. | |
| 6,531,239 B2 | 3/2003 | Heller | |
| 6,599,407 B2 | 7/2003 | Taniike et al. | |
| 6,740,215 B1 | 5/2004 | Nakaminami et al. | |

(Continued)

FOREIGN PATENT DOCUMENTS

| | | |
|---|---|---|
| DE | 301808 A1 | 11/1917 |
| DE | 41 26 692 A1 | 2/1993 |
| DE | 43 14 417 A1 | 11/1994 |
| DE | 43 44 646 A1 | 6/1995 |
| EP | 0745843 A2 | 12/1996 |
| JP | 55-78242 | 6/1980 |
| JP | 57-12359 | 1/1982 |
| WO | 89/06802 | 7/1989 |
| WO | 02/06828 A2 | 1/2002 |

OTHER PUBLICATIONS

Trudeau, F.; et al. Reagentless Mediated Laccase Electrode for the Detection of Enzyme Modulators, Analytical Chemistry, Mar. 1, 1997, vol. 69, No. 5, pp. 882-886.*

(Continued)

*Primary Examiner* — Alex Noguerola
*Assistant Examiner* — Gurpreet Kaur
(74) *Attorney, Agent, or Firm* — Edward J. Baba; Khin K. Chin; Bozicevic, Field & Francis LLP

(57) ABSTRACT

A method of determining the percentage of glycated hemoglobin in a blood sample is disclosed wherein at least one of the assay steps is performed electrochemically. The method includes determining the total amount of hemoglobin in a sample by electrochemically measuring, in an oxygen electroreduction reaction at a cathode, the amount of oxygen in the sample. Because the amount of oxygen dissolved in the sample is known, the total hemoglobin is determined by subtracting the amount of free oxygen from the total oxygen measured, recognizing the fast equilibrium $Hb+O_2 \leftrightarrows HbO_2$. This can be followed by determining the amount of glycated hemoglobin in the sample. The cathode reaction is accomplished by contacting the sample with an enzyme, the enzyme being a copper-containing enzyme having four copper ions per active unit. The family of these enzymes includes, for example, laccases and bilirubin oxidases. A device associated with such a process or method is also provided.

21 Claims, No Drawings

U.S. PATENT DOCUMENTS

| | | | |
|---|---|---|---|
| 6,746,582 | B2 | 6/2004 | Heller et al. |
| 6,766,817 | B2 | 7/2004 | da Silva |
| 6,885,196 | B2 | 4/2005 | Taniike et al. |
| 6,918,404 | B2 | 7/2005 | da Silva |
| 7,018,755 | B2 | 3/2006 | Ikegami et al. |
| 7,066,586 | B2 | 6/2006 | da Silva |
| 7,238,442 | B2 | 7/2007 | Heller |
| 2002/0172992 | A1 | 11/2002 | Heller |
| 2003/0152823 | A1 | 8/2003 | Heller |
| 2008/0044721 | A1 | 2/2008 | Heller et al. |

OTHER PUBLICATIONS

Tayhas, G.; et al. Electro-enzymatic reduction of dioxygen to water in the cathode compartment of a biofuel cell, Journal of Electroanalytical Chemistry, Mar. 19, 1999, vol. 464, pp. 110-117.*

Tsujimura, S; et al. Bioelectrocatalytic reduction of dioxygen to water at neutral pH using bilirubin oxidase as an enzyme and 2,2'-azinobis (3-ethylbenzothiazolin-6-sulfonate) as an electron transfer mediator, Journal of Electroanalytical Chemistry, Jan. 19, 2001, vol. 496, pp. 69-75.*

Frew, J. E.; et al. Electrochemical Biosensors, Analytical Chemistry, Aug. 1, 1987, vol. 59, pp. 933A-944A.*

Gorton, L.; Carbon Paste Electrodes Modified with Enzymes, Tissues, and Cells, Electroanalysis, Jan. 1995, Vo. 7, pp. 23-45.*

Taylor, C.; et al. "Wiring" of glucose oxidase within a hydrogel made with polyvinyl imidazole complexed with [(Os-4,4'-dimethoxy-2,2'-bipyridine)Cl], Journal of Electroanalytical Chemistry, Oct. 31, 1995, vol. 396, pp. 511-515.*

International Search Report, Jul. 19, 2002.

N. Kuroda, et al., "Determination of sugars and polyols in red blood cells by high-performance liquid chromatography with pulsed amperometric detection-2. Red blood cell myo-inositol", Dep. Of Clinical Laboratory, Kagawa Medical Sch., Japan, Tonyobyo (Tokyo), 1995, 38(12), pp. 979-983.

F.Lisdat, et al., "Laccase-modified thick film electrodes", (Germany) Technical Digest of the 7$^{th}$ International Meeting on Chemical Sensors, 1998, pp. 786-788.

W. F. M. Stöcklein and F. W. Scheller, "Laccase: A Marker Enzyme for Solvent-modified Immunoassays", Ann. N.Y. Acad. Sci., 1996, vol. 799, pp. 525-528.

F. F. Bier, et al., "An enzymatic amplification cycle for high sensitive immunoassay", Anal. Chim. Acta, 1996, vol. 328, No. 1, pp. 27-32.

F. F. Bier, et al., "High sensitive competitive immunodetection of 2,4-dichlorophenoxyacetic acid using enzymatic amplification with electrochemical detection", J. Anal. Chem., 1996, vol. 354, No. 7-8, pp. 861-865.

W. F. M. Stöcklein, et al., "Effects of organic solvents on semicontinuous immunochemical detection of coumarin derivatives", Sens. Actuators, vol. B 24(1-3), 1995, pp. 80-84.

Willner et al., "Integration of Layered Redox Proteins and Conductive Supports for Bioelectronic Applications," Angew. Chem. Int. Ed. (2000) 39:1180 -1218.

Ohara et al., "Glucose Electrodes Based on Cross-Linked [Os(bpy)2Cl] +/2+ Complexed Poly(1-vinylimidazole) Films," Anal. Chem. (1993) 65:3512-3517.

Fersht, Alan, "Structure and mechanism in protein science: a guide to enzyme catalysis and protein folding," Book, (1999) WH Freeman, pp. 473 and 474.

Cook, Paul, "Enzyme mechanism from isotope effects," Book, (1991) CRC Press, pp. 351-352.

Alkire, et al., "Current Distribution in a Tubular Electrode under Liminar Flow: One Electrode Reaction," J. Electrochem. Soc.: Electrochemical Science and Technology, vol. 124, No. 7, pp. 1043-1049.

Aoki, et al., "Electron Diffusion Coefficients in Hydrogels Formed of Cross-Linked Redox Polymers," The Journal of Physical Chemistry. 1993, vol. 97, pp. 11014-11019.

Aoki, et al., "Effect of Quaternization on Electron Diffusion Coefficients for Redox Hyrdrogels Based on Poly(4-vinylpyridine)," The Journal of Physical Chemistry. 1995, vol. 99, No. 14, pp. 5012-5110.

Barton, et al., "Electroreduction of O2 to Water on the 'Wired' Laccase Cathode," J. Phys. Chem. B. 2001, vol. 105, pp. 11917-11921.

Barton et al., "The 'Wired' Laccase Cathode: High Current Density Electroreduction of O2 to Water at +0.7 V (NHE) at pH 5," J. Am. Chem. Soc. 2001, vol. 123, pp. 5802-5803.

Barton et al., "Electroreduction of O2 to Water at 0.6 V (SHE) at pH 7 on the 'Wired' *Pleurotus ostreatus* Laccase Cathode," Biosensors and Bioelectronics. 2002, vol. 17, pp. 1071-1074.

Binyamin et al., "Mechanical and Electrochemical Characteristics of Composites of Wired Glucose Oxidase and Hydrophilic Graphite," Journal of the Electrochemical Society. 2000, vol. 147, No. 7, pp. 2780-2783.

Binyamin et al., "Stablilization of Wired Glucose Oxidase Anodes Rotating at 1000 rpm at 37° C," Journal of the Electrochemical Society, vol. 146, No. 8, pp. 2965-2967.

Blauch et al., "Effects of Long-Range Electron Transfer on Charge Transport in Static Assemblies of Redox Centers," The Journal of Physical Chemistry. 1993, vol. 97, No. 24, pp. 6444-6448.

Chen et al., "A Miniature Biofuel Cell," Journal of the American Chemical Society. 2001, vol. 123, No. 35, pp. 8630-8631.

Chen et al., "In Situ Assembled Mass-Transport Controlling Micromembranes and Their Application in Implanted Amperometric Glucose Sensors," Analytical Chemistry. Aug. 15, 2000, vol. 72, No. 16, pp. 3757-3763.

Colon et al., "Cobalt Polypyridyl Complexes as Redox Mediators for Lipoamide Dehydrogenase," Electroanalysis, 1998, vol. 10, No. 9, pp. 621-627.

Greenfield et al., "Inactivation of Immobilized Glucose Oxidase by Hydrogen Peroxide," Analytical Biochemistry. 1975, vol. 65, pp. 109-124.

Heller, "Electrical Connection of Enzyme Redox Centers to Electrodes," The Journal of Physical Chemistry. 1992, vol. 96, No. 9, pp. 3579-3587.

Jaremko et al., "Advances Toward the Implantable Artificial Pancreas for Treatment of Diabetes," Diabetes Care. Mar. 1998, vol. 21, No. 3, pp. 444-450.

Jin et al., "Electron Transfer Between Cytochrome C and Copper Enzymes," Biochemistry and Bioenergetics. 1996, vol. 39, pp. 221-225.

Katakis et al., "Electrostatic Control of the Electron Transfer Enabling Binding of Recombinant Glucose Oxidase and Redox Polyelectrolytes," Journal of the American Chemical Society. 1994, vol. 116, No. 8, pp. 3617-3618.

Katz et al., "A Non-Compartmentalized Glucose I O2 Biofuel Cell by Bioengineered Electrode Surfaces," Journal of Electroanalytical Chemistry. 1999, vol. 479, pp. 64-68.

Katz et al., "A Biofuel Cell Based on Two Immiscible Solvents and Glucose Oxidase and Microperoxidase-11 Monolayer-Functionalized Electrodes," New J Chem. 1999, pp. 481-487.

Kenausis et al., "'Wiring' of Glucose Oxidase and Lactate Oxidase Within a Hydrogel Made with Poly(vinyl pyridine) Complexed with $[Os(4,4'-dimethoxy-2,2'-bipyridine)_2 l]^{+2/2+}$," The Journal of the Chemical Society, Faraday Transactions 1996, vol. 92. No. 20, pp. 4131-4136.

Koroljova-Skorobogatko et al., "Purification and Characterization of the Constitutive Form of Laccase from the Basidiomycete Coriolus Hirsutus and Effect of Inducers on Laccase Synthesis," Biotechnol Appl Biochem. 1998, vol. 28, pp. 47-54.

Lee et al., "Catalysis of the Reduction of Dioxygen at Graphite Electrodes Coated with Fungal Laccase A," J. Electroanal. Chem. 1984, col. 172, pp. 289-300.

De Lumley-Woodyear et al., "Polyacrylamide-Based Redox Polymer for Connecting Redox Centers of Enzymes to Electrodes," Analytical Chemistry. 1995, vol. 67, No. 8, pp. 1332-1338.

Mano et al., "A Miniature Biofuel Cell Operating in a Physiological Buffer," J Am Chem Soc. 2002, vol. 124, pp. 12962-12963.

Mano et al., "On the Relationship Between the Characteristics of Bilirubin Oxidases and O2 Cathodes Based on Their 'Wiring'," J Phys Chem B. 2002, vol. 106, pp. 8842-8848.

Mano et al., "*An Oxygen Cathode Operating in a Physiological Solution*," J. Am. Chem. Soc. 2002,124, 6480-6486.

Mano et al. "A Miniature Biofuel Cell Operating at 0.78 V," Chem Commun. 2003, pp. 518-519.

Ohara et al., "'Wired' Enzyme Electrodes for Amperometric Determination of Glucose or Lactate in the Presence of Interfering Substance," Analytical Chemistry. Aug. 1, 1994, vol. 66, No. 15, pp. 2451-2457.

Palmore et al., "Electro-Enzymatic Reduction of Dioxygen to Water in the Cathode Compartment of a Biofuel Cell," Journal of Electroanalytical Chemistry. 1999, vol. 464, pp. 110-117.

Palmore et al., "A Methanol/Dioxygen Biofuel Cell that uses $NAD^+$-Dependent Dehydrogenases as Catalysts: Application of an Electro-Enzymatic Method to Regenerate Nicotinamide Adenine Dinucleotide at Low Overpotentials," Journal of Electroanalytical Chemistry. 1998, vol. 443, pp. 155-161.

Palmore et al., "Microbial and Enzymatic Biofuel Cells," Enzymatic Conversion of Biomass for Fuels Production, 1994, Chapter 14, pp. 271-290.

Quinn et al., "Biocompatible, Glucose-Permeable Hydrogel for in situ Coating of Implantable Biosensors," Biomaterials. 1997, vol. 18, No. 23, pp. 1665-1670.

Quinn et al., "Photo-Crosslinked Copolymers of 2-Hydroxyethyl Methacrylate, Poly(ethylene Glycol) Tetra-Acrylate and Ethylene Dimethacrylate for Improving Biocompatibility of Biosensors," Biomaterials. 1995. vol. 15. No. 5. pp. 389-396.

Rajagopalan et al., "Effect of Quaternization of the Glucose Oxidase 'Wiring' Redox Polymer on the Maximum Current Densities of Glucose Electrodes," The Journal ofPhysical Chemistry. 1996, vol. 100, No. 9, pp. 3719-3727.

Rajagopalan et al., "Electrical 'Wiring' of Glucose Oxidase in Electron Conducting Hydrogels," Molecular Electronics, Chapter 7, pp. 241-254.

Rao et al., "Metal-Oxygen and Glucose-Oxygen Cells for Implantable Devices," Biomedical Engineering. 1974, vol. 9, No. 3, pp. 98-102.

Santucci et al., "Unmediated Heterogeneous Electron Transfer Reaction of Ascorbate Oxidase and Laccase at a Gold Electrode," Biochem. J. 1990, vol. 332, pp. 611-615.

Sayka et al., "The Effect of Plasma Treatment on the Wettability of Substrate Materials," Solid State Technology. 1989, vol. 32, No. 5, pp. 69-70.

Service, "Can Chip Devices Keep Shrinlung?" Science. Dec. 13, 1996, vol. 274, pp. 1834-1836.

Tarasevich et al., "Electrocatalysis of Cathodic Molecular Oxygen Reduction with Biopolymers-Enzymes and Their Models," J. Electroayal. Chem. 1986, vol. 206, pp. 217-227.

Tarasevich et al., "Electrocatalysis of a Cathodic Oxygen Reduction by Laccase," Bioelectrochemistry and Bioenergetics. 1979, vol. 6, pp. 393-403.

Taylor, "'Wiring' of Glucose Oxidase Within a Hydrogel Moade with Polyvinyl Imidazole Complexed with $[Os-4,4'\text{-dimethoxy-2,2'-bipyridine})Cl]^{+/2+}$," Journal of Electroanalytical Chemistry. 1995, vol. 396. pp. 511-515.

Thuesen et al., "Cyclic Voltammetry and Electrocatalysis of the Blue Copper Oxidase Polyporous Versicolor Laccase," Acta Chemica Scandinavica. 1998, vol. 52, pp. 555-562.

Trudeau et al., "Reagentless Mediated Laccase Electrode for the Detection of Enzyme Modulators," Analytical Chemistry. Mar. 1, 1997, vol. 69, No. 5, pp. 882-886.

Tsujimura et al., "Bioelectrocatalytic Reduction of Dioxygen to Water at Neutral pH Using Bilirubin Oxidase as an Enzyme and 2,2'-Azinobis (3-ethylbenzothiazolin-6-sulfonate) as an Electron Transfer Mediator." Journal of Electroanalytical Chemistry. 2001, vol. 496, pp. 69-75.

Tsujimura et al., "Glucose/02 Biofuel Cell Operating at Physiological Conditions," Electrochemistry. 2002, vol. 70, No. 12, pp. 940-942.

Vreeke et al., "Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network," Analytical Chemistry. Dec. 15, 1992, vol. 64, No. 24, pp. 3084-3090.

Wagner et al., "Continuous Amperometric Monitoring of Glucose in a Brittle Diabetic Chimpanzee with a Miniature Subcutaneous Electrode," Proc. Natl. Acad. May 1998, vol. 95, pp. 6379-6382.

Willner et al., "A Biofuel Cell Based on Pyroloquinoline Quinone and Microperoxidase-11 Monolayer-Functionalized Electrodes," Bioelectrochemistry and Bioenergetics. 1998, vol. 44, pp. 209-214.

Willner et al., "Biofuel Cell Based on Glucose Oxidase and Microperoxidase-11 Monolayer-Functionalized Electrodes," Journal of the Chemical Society—Perkin Transactions. 1998, vol. 2, No. 8, pp. 1817-1822.

Yahiro et al., "Bioelectrochemistry I. Enzyme Utilizing Bio-Fuel Cell Studies," Biochimica et Biophysica Acta. 1964, vol. 88, pp. 375-383.

Yaropolov et al., "Electrochemical properties of Some Copper-Containing Oxidases," Bioelectrochemistry and Bioenergetics. 1996, vol. 40, pp. 49-57.

Ye et al., "High Current Density 'Wired' Quinoprotein Glucose Dhydrogenase Electrode," Analytical Chemistry. Feb. 1, 1993, vol. 65, No. 3, pp. 238-241.

Zakeeruddin et al., "Towards Mediator Design: Characterization of Tris-(4,4'-substituted-2,2'-bipyridine) Complexes of Iron(II), Ruthenium(II) and Osmium(II) as Mediators for Glucose Oxidase of *Aspergillus niger* and Other Redox Proteins," J. Electroanal. Chem. 1992. vol. 337, pp. 253-283.

(Author Unknown), "Hemoglobin Function" Ch. 3, pp. 37-60 (date unkown).

Notification of Transmittal of International Preliminary Examination Report, mailed Oct. 7, 2004, in International Application No. PCT/US03113806 of TheraSense, Inc.

Notification of Transmittal of the International Search Report of the Declaration, mailed May 11, 2004, in International Application No. PCTUS03113806 of TherSense, Inc.

* cited by examiner

DEVICE FOR THE DETERMINATION OF GLYCATED HEMOGLOBIN

CROSS-REFERENCE TO RELATED APPLICATIONS

This application is a continuation of U.S. application Ser. No. 10/146,577, entitled "Method for the Determination of Glycated Hemoglobin", filed May 14, 2002, now U.S. Pat. No. 7,005,273 which claims priority from U.S. provisional patent application No. 60/291,361, entitled "Biofuel Cell," filed May 16, 2001, as well as U.S. provisional application No. 60/377,886, entitled "Miniature Biological Fuel Cell That is Operational Under Physiological Conditions", filed May 2, 2002, naming inventors Heller, Mano, Kim, Zhang and Mao, the contents of which applications are incorporated herein by reference in their entireties.

BACKGROUND

1. Field of the Invention

The present invention relates to a process for the determination of the amount of irreversibly glycated hemoglobin, or HbA1c, present in a sample of blood, relative to the amount of total hemoglobin. In particular, the invention incorporates in the method an electrochemical, enzyme-catalyzed reaction or reactions. The present invention also relates to devices associated with such processes or methods.

2. Background Information

HbA1c is a glycated hemoglobin formed by a binding reaction between an amine group of hemoglobin and the glucose aldehyde group, for example between the amino group of the N-terminal valine of the β-chain of hemoglobin and the glucose aldehyde group. The binding reaction first forms a Schiff's base and then a stable ketoamine by Amadori rearrangement. The percentage of HbA1c (i.e. the amount of glycated hemoglobin relative to total hemaglobin in the blood) has come to be taken as a measure of the level of blood glucose control a diabetic patient has maintained for a period of two or three months prior to the measurement. As such, percentage HbA1c has become an important measurement by which health care providers can assist diabetic patients in their care.

There are many known assays that can be used to determine HbA1c percentage. In recent years research efforts have focused on creating assays that are both highly accurate and fast. However, known HbA1c assays typically require a substantial number of time-consuming steps wherein the blood components must be separated and treated.

In the health care context, a diabetic patient is typically guided by a physician to obtain an HbA1c measurement when the physician realizes that there is a need for such information during an office visit. The patient then provides a blood sample to a laboratory and results are returned to the physician hours or days later. Typically, the lab will use a table top analyzer of the type presently available commercially. This time lag between the patient's visit and the result of the test requires that the physician review the result long after the patient has left the office. If the physician believes that further consultation with the patient is required in light of the test result, the patient must be contacted again.

Currently, there is a device sold under the name "A1c NOW" by Metrika, Inc. of Sunnyvale, Calif. This handheld and disposable device (based on technology described in U.S. Pat. No. 5,837,546 entitled "Electronic Assay Device and Method," incorporated herein by reference) is said to provide an HbA1c test result in eight minutes using a relatively small sample of blood. The A1c NOW device is an example of the market demand for a fast method of providing an HbA1c result for either home or doctor's office use. However, the A1c NOW device is not as accurate as some laboratory assays. Thus, research has continued to focus on finding a highly accurate HbA1c assay that is also fast enough and simple enough to permit a diabetic and his or her doctor to take a blood sample during an office visit and have a trustworthy HbA1c measurement available for discussion in the same visit.

SUMMARY OF THE INVENTION

The present invention comprises a method of determining the amount or percentage of glycated hemoglobin in blood or a sample derived from blood, in which at least one of the assay steps is performed electrochemically. The use of electrochemical methodology can retain or improve the accuracy of other methods and potentially speed the ultimate determination. Devices providing electrochemical measurements can also be relatively small.

In one embodiment, the method includes electrochemically determining the total amount of hemoglobin in a sample by electrochemically measuring, in an oxygen electroreduction reaction at a cathode, the amount of oxygen in the sample, preferably after it was exposed to air so as to assure that the hemoglobin is oxygenated. Because the amount of oxygen dissolved in aerated physiological buffer at the assay temperature in the absence of hemoglobin, termed here free oxygen, is known, the total hemoglobin may be determined by subtracting the amount of free oxygen from the total oxygen measured, recognizing the fast equilibrium $Hb+O_2 \leftrightarrows HbO_2$. Electrochemically determining the total hemoglobin value can be followed by a determination of the amount of glycated hemoglobin in the sample. In the process of the invention, the cathode reaction is accomplished by contacting the sample with an enzyme. In this embodiment, the enzyme can be a copper-containing enzyme, containing four copper ions per active unit. The family of these enzymes includes, for example, laccases and bilirubin oxidases.

The glycated hemoglobin can be determined in different ways. In one embodiment, the glycated hemoglobin is separated from the sample, for example by capturing it with immobilized antibodies against HbA1c or with a boronic acid modified surface. Examples of surfaces include those of small magnetic, polymer or glass beads. The percentage HbA1c can then be determined by either measuring the hemoglobin left in the sample from which the HbA1c has been removed, or by measuring the amount of glycated hemoglobin in the separated portion of the sample. The amount of glycated hemoglobin can be measured spectrophotometrically, or by an electrochemical measurement in the same manner as the total hemoglobin. In another embodiment the hemoglobin is hydrolyzed by an established method, such as digestion with a proteolytic enzyme. The ketoamines in the hydrolyzate, such as the fragments comprising the Amadori rearrangement products of the Schiff base formed of amino acids, including valine and glucose, are then determined, preferably by an electrochemical method. In the electrochemical method, the electrooxidation of the hydrolyzed Amadori rearrangement product may be catalyzed by an enzyme and a dissolved or immobilized redox mediator. The enzyme can be, for example, a fructosamine oxidase, a four copper-ion containing copper enzyme such as a laccase or a bilirubin oxidase, ceruloplasmin, or ascorbate oxidase. The redox mediators can be, for example, complexes of $Os^{2+/3+}$, or of $Ru^{2+/3+}$.

The present invention also comprises a device associated with processes or methods disclosed herein.

DETAILED DESCRIPTION

The invention incorporates one or more electrochemical steps in the method of determining percentage HbA1c. The method of the invention is based on the understanding that hemoglobin, being the oxygen carrier of blood, reversibly binds oxygen, forming $HbO_2$. The equilibrium $Hb+O_2 \leftrightarrows HbO_2$ is rapid. Because $O_2$ is rapidly released by $HbO_2$ when $O_2$ is depleted from the solution in an electrochemical cell, it is possible to determine the concentration of $HbO_2$ in light of the reaction $4H^+ + 4e^- + HbO_2 \rightarrow 2H_2O + Hb$.

Determining Total Hemoglobin Electrochemically

In the invention, it may be useful to pre-treat a blood sample by collecting the relatively large blood cells on a filtration membrane. After rinsing the collected cells with saline to remove adhering proteins, the cell membranes may be ruptured by exposing them to deionized water or a detergent. In this manner, the dissolved hemoglobin will pass the filtration membrane. The cell membranes will remain on the filter paper.

In a preferred form of the invention, total hemoglobin is then determined from the sample by electroreducing the oxygen bound to the hemoglobin to water at the cathode in an electrochemical cell. The oxygen electroreduction catalyst preferably comprises a so-called "copper" enzyme such as bilirubin oxidase, a laccase, or an ascorbate oxidase.

The catalyst may further comprise a redox mediator to form a "wired enzyme" arrangement. In this system, the electrical connection is between a cathode of the electrochemical cell and the oxygen reduction catalyzing enzyme, especially a copper-containing enzyme, such as bilirubin oxidase (sometimes referenced herein as BOD). Thus, in one form of the invention, it is preferred to "wire" reaction centers of an enzyme, e.g. bilirubin oxidase, to a cathode. Bilirubin oxidase catalyzes the four-electron reduction of oxygen to water. A cathode constructed with bilirubin oxidase is especially preferred as the redox enzyme can function under relatively neutral pH conditions. However, other enzymes (e.g. lacasse) may be useful in the method of the invention so long as they provide catalytic functionality for the reduction of oxygen to water.

Thus, the concentration of $HbO_2$ can be measured by the reaction $4H^+ + 4e^- + HbO_2 \rightarrow 2H_2O + Hb$. This measurement may be done coulometrically. The concentration of available oxygen in arterial blood tends to be about 8 mM. Because the concentration of $O_2$ in water in equilibrium with air at 25° C. is known (the concentration is generally around 0.24 mM), the amount of non-Hb bound $O_2$ can then be subtracted in calculating the amount of $HbO_2$.

A cathode useful in the invention effectuates the four-electron electroreduction of $O_2$ to water. The blue, copper-containing oxidases, examples of which include laccases, ascorbate oxidase, ceruloplasmine, and bilirubin oxidase, catalyze the four-electron reduction of $O_2$ to water. The preferred enzymes are exemplified by bilirubin oxidases, which unlike laccases, retain their more than 80%, and usually retain more than 90%, of the maximal activity under physiological pH. The catalytic reduction of $O_2$ to water depends on the coordination of the four $Cu^{+/2+}$ ions of the enzymes. The $Cu^{+/2+}$ ions are classified, by their ligands, into three "types", types 1, 2, and 3. Type 1 $Cu^{+/2+}$ centers show an intense Cys S to Cu(2) charge transfer band at around 600 nm; the site accepts electrons from an organic substrate, such as a phenol, ascorbate, or bilirubin, and relays the electrons to the $O_2$-reduction site. The $O_2$-reduction site is a trinuclear cluster, consisting of one type 2 $Cu^{+/2+}$ center and a pair of type 3 $Cu^{+/2+}$ centers, their spectrum showing a shoulder at 330 nm.

There are different forms of bilirubin oxidase available, such as bilirubin oxidase from *Myrothecium verrucaria* (Mv-BOD) and bilirubin oxidase from *Trachyderma tsunodae* (Tt-BOD). Bilirubin oxidases are usually monomeric proteins and have molecular weights approximately ranging from about 52 kDa to about 65 kDa. Tt-BOD is a monomeric protein with a molecular weight of approximately 64 kDa, while that of Mv-BOD is about 52 kDa. Both Mv-BOD and Tt-BOD are multicopper oxidases, each containing one type 1, one type 2, and two type 3 copper ions. These three types are defined by their optical and magnetic properties. Type 1 (blue) copper ions have a characteristic Cys to Cu(2) charge-transfer band near 600 nm. The type 1 copper center accepts electrons from the electron-donating substrate of the enzyme and relays these to the $O_2$ reduction site. The latter is a trinuclear cluster, consisting of a type 2 copper ion and a type 3 pair of cupric ions with a characteristic 330 nm shoulder in its absorption spectrum.

In one embodiment of the invention, bilirubin oxidase from *Myrothecium verrucaria* could be used in a cathode electrocatalyst layer. In a cathode constructed using Mv-BOD, the electrostatic adduct of the poly-anionic Mv-BOD and its "wire", the polycationic redox copolymer of polyacrylamide (PAA) and poly (N-vinylimidazole) (PVI) complexed with [Os (4,4'-dichloro-2,2'-bipyridine)$_2$Cl]$^{+/2+}$, are immobilized on the cathode.

In another embodiment of the invention, bilirubin oxidase (BOD) from *Trachyderma tsunodae* can be used in a cathode electrocatalyst layer. In Tt-BOD all of the ligands of the Type 2 and Type 3 $Cu^{+/2+}$ centers are His (histidines), similar to ascorbate oxidase. It is believed that the full histidine coordination of the type 2 $Cu^{+/2+}$ center is the underlying cause of the relative insensitivity of bilirubin oxidases to inhibition by the chloride and hydroxide anions (as are found at physiological concentration). Accordingly, it is expected that other enzymes having the three types of copper centers would also be useful as components of cathode electrocatalysts in cathodes operating under at near neutral pH.

The redox potentials of the redox polymers that "wire" the cathode enzyme can be tailored for use in the invention. Redox polymers for use in the method may include PAA-PVI-[Os(4,4'-dichloro-2,2'-bipyridine)$_2$Cl]$^{+/2+}$ which can be prepared as follows: 4,4'-Dinitro-2,2-bipyridine N,N'-dioxide was prepared as described in Anderson, S.; Constable, E. C.; Seddon, K. R.; Turp, E. T.; Baggott, J. E.; Pilling, J. *J. Chem. Soc., Dalton Trans.* 1985, 2247-2250, and Kenausis, G.; Taylor, C.; Rajagopalan, R.; Heller, A. *J. Chem. Soc., Faraday Trans.* 1996, 92, 4131-4135. 4,4'-dichloro-2,2'-bipyridine (dcl-bpy) was synthesized from 4,4'-dinitro-2,2'-bipyridine N,N'-dioxide by modifying the procedure of Maerker et al. (see Anderson, S., supra and Maerker, G.; Case, F. H. *J. Am. Chem. Soc.* 1958, 80, 2475-2477.). Os(dcl-bpy)$_2$Cl$_2$ was prepared as follows: (NH$_4$)$_2$OsCl$_6$ and "dcl-bpy were dissolved in ethylene glycol in a 1:2 molar ratio and refluxed under argon for 1 hour (yield 85%). The Os(dcl-bpy)$_2$Cl$_2$ was then complexed with the 1:7 polyacrylamide-poly(N-vinylimidazole) (PAA-PVI) copolymer and purified as described in Zakeeruddin, S. M.; D. M. Fraser, D. M.; Nazeeruddin, M.-K.; Gratzel, M. *J. Electroanal. Chem.* 1992, 337, 253-256 to form the PAA-PVI-[Os(4,4'-dichloro-2,2'-bipyridine)$_2$Cl]$^{+/2+}$ redox polymer. Those skilled in the art are aware of numerous variations that can be prepared and used as redox polymers according to the invention.

Determination of the HbA1c Percentage

Once the total hemoglobin has been measured, the HbA1c/Hb ratio can be determined by separating the HbA1c fraction from the sample. The HbA1c, which can be converted to HbA1cO2, can then be measured indirectly and electrochemically using the same method as for the total hemoglobin. Alternatively, these fructosyl amines may be subject to direct enzyme catalyzed electro-oxidation, for example using fructosyl amine oxidases having FAD/FADH reaction centers, or by one of the copper enzymes.

The following are examples of suitable methods which incorporate the separation and HbA1c assay steps.

EXAMPLE 1

Affinity gel columns can be used to separate bound, glycosylated hemoglobin from the nonglycosylated fraction. The gel contains immobilized m-aminophenylboronic acid on cross-linked, beaded agarose. The boronic acid first reacts with the cis-diol groups of glucose bound to hemoglobin to form a reversible 5-membered ring complex, thus selectively holding the glycosylated hemoglobin on the column. Next, the nonglycosylated hemoglobin is eluted. The ring complex is then dissociated by sorbitol, which permits elution of the glycosylated hemoglobin. Using affinity chromatography, absorbances of the bound and nonbound fractions, measured at 415 nm, are used to calculate the percent of glycosylated hemoglobin.

EXAMPLE 2

Magnetic beads that are <1 μm (available from Bangs Laboratories), on which antibodies against HbA1c would be immobilized, can be mixed with a citrate-solution diluted blood sample. Two measurements are performed, one on the entire sample, and a second on the re-oxygenated Hb1Ac bound to the magnetic beads, after their removal to a chamber of an electrochemical cell. Alternatively, the second measurement can be on the residual Hb, after the magnetic separation of the bead-bound HbA1c.

EXAMPLE 3

Two samples of the lysed red blood cells in citrate buffer can be coulometrically assayed in two chambers. In Chamber 1, the total $HbO_2$ would be measured. Chamber 2 contains the immobilized HbA1c-specific antibody. Either of the two would capture HbA1c without capturing Hb. After rinsing or passage of citrate buffer through Chamber 2 (e.g. by repeated filling through capillary action and touching the edge of the chamber to filter paper), the chamber would contain only $HbA1cO_2$. The $HbA1cO_2$ would be assayed electrochemically (preferably coulometrically) by its electroreduction, $4H^+ + 4e^- + HbA1cO_2 \rightarrow 2H_2O + HbA1c$. The HbA1c/Hb ratio can then be calculated from the two coulometric measurements.

EXAMPLE 4

As in example 3 above, except that the two coulometric measurements would be performed in a single chamber. The chamber, which would contain the immobilized HbA1c capture agent, would be filled with a citrate solution of the lysed red blood cells. First, the total $HbO_2$ would be electrochemically (preferably coulometrically) measured. Next, the unbound Hb, but not the bound HbA1c, would be rinsed out, the HbA1c would be re-equilibrated with air, and its amount would be coulometrically measured.

Thus, the assay of the invention, in one form, can comprise a method of determining the ratio of HbA1c to total Hb in blood, the method comprising obtaining a blood sample; electrochemically determining the total amount of hemoglobin in the sample, or in a treated portion of the sample; electrochemically determining the amount of HbA1c in the sample; and calculating the ratio of HbA1c to total hemoglobin. In a preferred form the method of electrochemically determining the total amount of hemoglobin in the sample is accomplished by placing the sample in an electrochemical cell in which, at the cathode, a cathode enzyme is bound, for example using a redox polymer. In this method, it is preferred that the enzyme be a laccase or a bilirubin oxidase which will electroreduce oxygen bound to the hemoglobin to water. The hemoglobin content is determined from the oxygen content.

In another form of the invention the electrochemical determination of HbA1c fraction can be accomplished by one of two methods. In a first method, the A1c containing fraction of the hemoglobin is separated by physical means, such as by use of an HbA1c specific antibody. Under appropriate conditions the HbA1c then present in the form of $HbA1cO_2$ can then be electrochemically determined by electroreduction of the oxygen. (again with an enzyme selected to accomplish the four electron reduction of oxygen). In a second method, the glycated protein (a fructosyl amine) can be directly oxidized on cross-linked poly(N-vinyl imidazole) based redox polymer films (without an enzyme) of sufficiently positive oxidizing potential. Alternatively, enzymatic electrooxidation of the fructosyl amines can be used for this part of the determination.

Finally, the invention comprises an electrochemical method for the determination of HbA1c (or HbA1c/Hb ratio) comprising determining from a starting sample, in an electrochemical cell, the total amount of hemoglobin (e.g. by measuring bound oxygen), separating the HbA1c component from the sample using an HbA1c capturing agent, and measuring hemoglobin content in the captured or non-captured portion of the sample.

Devices for accomplishing the method of the invention are preferably small. By incorporating electrochemical steps, it may be possible to prepare biosensor strips which include a cathode at which the chemistry discussed herein is placed, as well at which the necessary anode is constructed. Such strips can be prepared using techniques presently used for making commercially available biosensor strips that are used for glucose determinations, such as the FreeStyle blood glucose system sold by TheraSense, Inc. Samples could then be applied to these strips and the strips placed in the measuring instrument (meter) to be "read." By constructing a portion of the equipment in the form of electrochemical biosensor strips, the electrochemical method of the invention provides a significant potential advantage of creating a smaller analysis device while providing accurate results.

What is claimed is:

1. A device for use in electrochemically assaying glycated hemoglobin in a blood, blood-containing, or blood-derived sample, comprising:
   a first chamber and a second chamber separate from the first chamber, wherein the first and second chambers comprise:
     a cathode comprising an enzyme capable of reducing oxygen to water and a redox mediator, wherein the enzyme and the redox mediator are immobilized on the cathode by a polymer, wherein the redox mediator and the polymer form a redox polymer, and an anode, and wherein the second chamber further comprises a surface-immobilized glycated hemoglobin separating agent or a glycated hemoglobin hydrolysis agent.

2. The device of claim 1, wherein the enzyme is a four copper-ion containing copper enzyme.

3. The device of claim 2, wherein the four copper-ion containing copper enzyme is selected from a laccase, a bilirubin oxidase, ceruloplasmin and ascorbate oxidase.

4. The device of claim 3, wherein the enzyme is a bilirubin oxidase.

5. The device of claim 4, wherein the redox polymer is polyacrylamide-poly(n-vinylimidazole)-[Os(4,4'-dichloro-2,2'-bipyridine)$_2$Cl]$^{+/2}$ (PAA-PVI-[Os(4,4'-dichloro-2,2'-bipyridine)$_2$Cl]$^{+/2+}$).

6. The device of claim 1 comprising a glycated hemoglobin hydrolysis agent.

7. The device of claim 6, wherein the glycated hemoglobin hydrolysis agent is a proteolytic enzyme.

8. The device of claim 7, comprising an enzyme that oxidizes ketoamines.

9. The device of claim 8, wherein the enzyme that oxidizes ketoamines is selected from a fructosamine oxidase and a four copper-ion containing copper enzyme.

10. The device of claim 9, further comprising a redox mediator.

11. The device of claim 10, wherein the redox mediator is an $Os^{2+/3+}$ or $Ru^{2+/3+}$ complex.

12. The device of claim 1 comprising a surface-immobilized glycated hemoglobin separating agent.

13. The device of claim 12, wherein the separating agent is selected from an anti-glycated hemoglobin antibody and a boronic acid-modified surface.

14. The device of claim 13, wherein the boronic acid modified surface is selected from magnetic, polymer or glass beads.

15. The device of claim 12, further comprising an enzyme that oxidizes fructosyl amines.

16. The device of claim 15, wherein the enzyme is selected from a fructosyl amine oxidase or a four copper-ion containing copper enzyme.

17. The device of claim 12, further comprising an cross-linked polyN-vinyl imidazole based redox polymer film.

18. The device of claim 12, further comprising a glycated hemoglobin hydrolysis agent.

19. The device of claim 18, wherein the glycated hemoglobin hydrolysis agent is a proteolytic enzyme.

20. The device of claim 19, further comprising an enzyme that oxidizes ketoamines.

21. The device of claim 20, wherein the enzyme that oxidizes ketoamines is selected from a fructosamine oxidase and a four copper ion containing copper enzyme.

* * * * *